United States Patent [19]

George et al.

[11] Patent Number: 4,810,711

[45] Date of Patent: *Mar. 7, 1989

[54] 1-(ACYLAMINOMETHYL)IMIDAZO(1,2-A)QUINOLINE DERIVATIVES, THEIR PREPARATION AND THEIR APPLICATION IN THERAPY

[75] Inventors: Pascal George, Vitry sur Seine; Daniéle De Peretti, Antony, both of France

[73] Assignee: Synthelabo, France

[*] Notice: The portion of the term of this patent subsequent to Jun. 23, 2004 has been disclaimed.

[21] Appl. No.: 5,823

[22] Filed: Jan. 21, 1987

[30] Foreign Application Priority Data

Jan. 22, 1986 [FR] France .................. 86 00835

[51] Int. Cl.⁴ .................. C07D 471/04; A61K 31/44
[52] U.S. Cl. .................. 514/292; 546/84; 546/121
[58] Field of Search .................. 546/84; 514/292

[56] References Cited

U.S. PATENT DOCUMENTS 4,650,796 3/1987 George et al. .................. 514/213
4,675,323 6/1987 George et al. .................. 514/292

Primary Examiner—Alan L. Rotman
Attorney, Agent, or Firm—Wegner & Bretschneider

[57] ABSTRACT

A compound which is a 1-acylaminomethylimidazo[1,2-a]quinoline of formula (I)

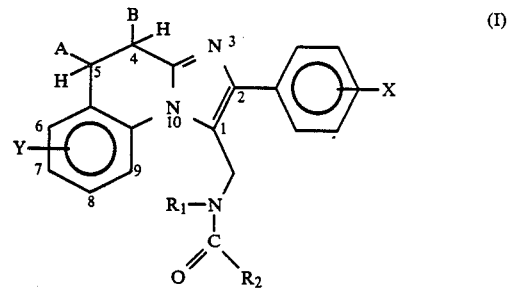

in which

A and B both denote hydrogen or together denote a direct carbon-carbon bond,

X denotes hydrogen or a halogen or a $(C_{1-4})$alkyl, $(C_{1-4})$alkoxy, $(C_{1-4})$alkylthio, methylsulphonyl, amino, $(C_{1-4})$alkylamino, di$(C_{1-4})$alkylamino, nitro or trifluormethyl group, Y denotes hydrogen or a halogen or a methyl group and is attached to the aryl ring at position 6, 7 or 8, $R_1$ denotes hydrogen or a $(C_{1-4})$alkyl group, and $R_2$ denotes a $(C_{1-6})$alkyl group, or a pharmaceutically acceptable acid addition salt thereof is useful in therapy.

10 Claims, 1 Drawing Sheet

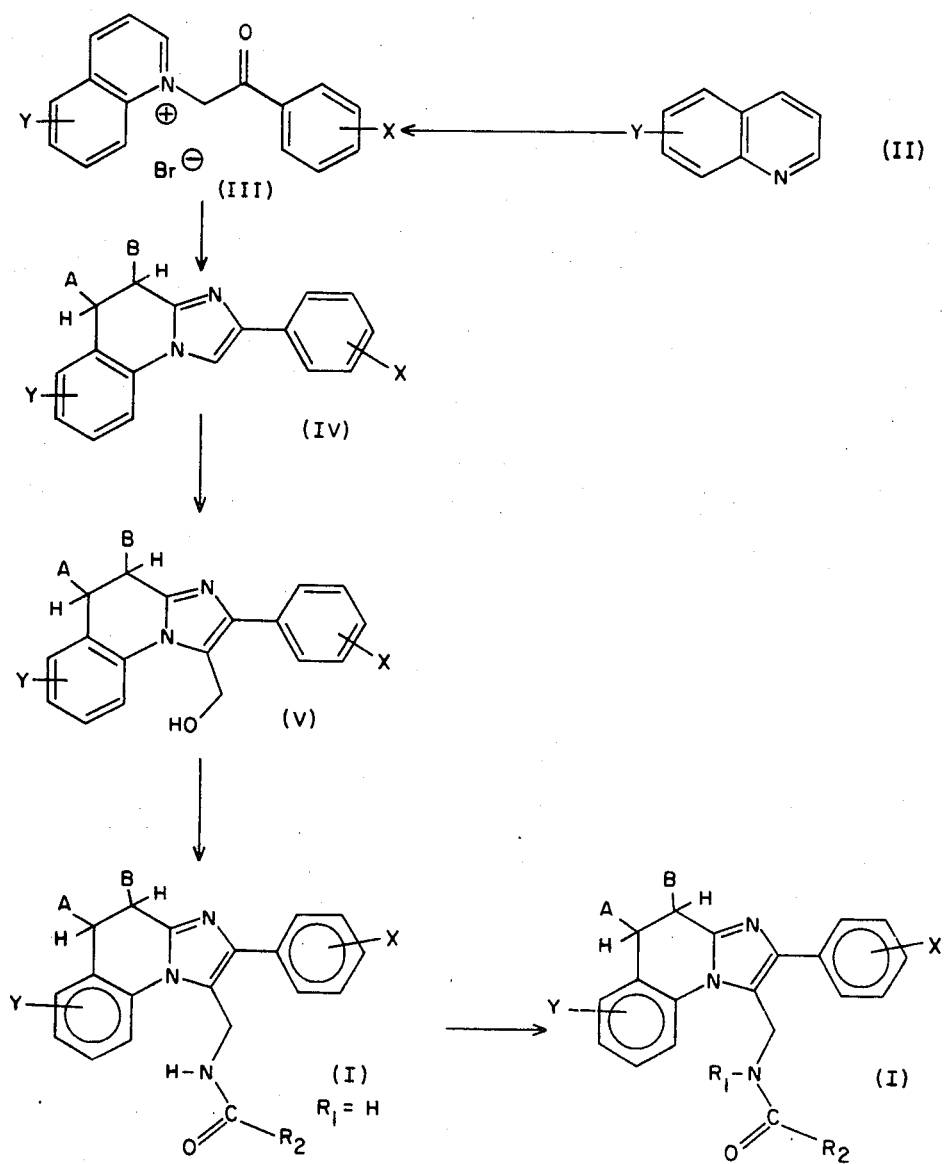

1-(ACYLAMINOMETHYL)IMIDAZO(1,2-A)QUINOLINE DERIVATIVES, THEIR PREPARATION AND THEIR APPLICATION IN THERAPY

The present invention provides compounds for use in therapy.

The present invention provides a compound which is a 1-acylaminomethylimidazo[1,2-a]quinoline of formula (I)

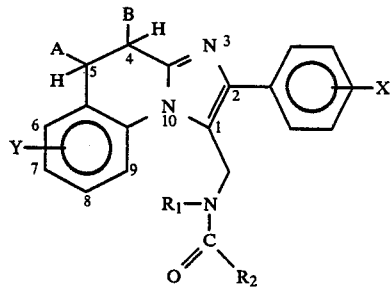

in which

A and B both denote hydrogen or together denote a direct carbon-carbon bond,

X denotes hydrogen or halogen or a $(C_{1-4})$alkyl, $(C_{1-4})$alkoxy, $(C_{1-4})$alkylthio, methylsulphonyl, amino, $(C_{1-4})$alkylamino, di$(C_{1-4})$alkylamino, nitro or trifluoromethyl group, Y denotes hydrogen or a halogen or a methyl group and is attached to the aryl ring at position 6, 7 or 8, $R_1$ denotes hydrogen or a $(C_{1-4})$alkyl group, and $R_2$ denotes a $(C_{1-6})$alkyl group, or a pharmaceutically acceptable acid addition salt thereof.

The alkyl groups can be linear or branched.

The preferred compounds of the invention are those in which

X is chlorine or a methyl or methylthio group,
Y is hydrogen, and
$R_1$ is hydrogen or a methyl group.

The present invention also provides a process for the preparation of a compound of formula (I) as shown in the attached drawing.

A quinoline of formula (II) is reacted with an α-bromoacetophenone bearing the substituent X as defined above, preferably at elevated temperature in a solvent such as methylene chloride or 1,2-dichloroethane. An ionic compound of formula (III) is obtained, which is then cyclized, generally under the action of heat, for example in the presence of ammonium acetate, in an organic solvent such as acetic or propionic acid, at a temperature of 90° C., to obtain a compound of formula (IV) in which A and B are hydrogen, or in the presence of ammonium acetate and ferric chloride, in a solvent such as acetic or propionic acid, at a temperature of 120° to 140° C., to obtain a compound of formula (IV) in which A and B together denote a direct carbon-carbon bond.

The compound of formula (IV) is then hydroxymethylated at position 1, for example by using an excess of formaldehyde in acetic acid. The alcohol of formula (V) obtained is reacted with a nitrile of formula $R_2CN$, generally in the presence of concentrated sulphuric acid and, after hydrolysis, the compound of formula (I) is obtained in which $R_1$ is hydrogen. This compound can optionally be alkylated, for example by using an alkyl iodide of formula $R_1I$, to provide a compound of formula (I) wherein $R_1$ is a $(C_{1-4})$alkyl group.

The examples which follow further illustrate the invention. Microanalyses and the IR and NMR spectra confirm the structure of the compounds.

EXAMPLE 1

N-methyl-N-{[2-(4-methylphenyl)-4,5-dihydroimidazo[1,2-a]quinol-1-yl]methyl}butanamide

1.1. 1-[2-(4-methylphenyl)-2-oxoethyl]quinolinium bromide 110 g (0.516 mol) of α-bromo-para-methylacetophenone and 61 ml (0.516 mol) of quinoline were dissolved in 500 ml of methylene chloride. The solution was heated at the reflux temperature for 1 hour and then diluted with 300 ml of ether and cooled. A yellow precipitate was obtained, which was filtered off and dried, of melting point 220°–221° C.

1.2. 2-(4-methylphenyl)-4,5-dihydroimidazo[1,2-a]-quinoline 17.1 g (0.05 mol) of the quaternary salt obtained in 1.1. and 25 g of ammonium acetate were mixed in 50 ml of acetic acid. This suspension was heated at 90° C. for 3 hours and then cooled. 200 ml of water were added and the brown precipitate filtered off, which was taken up with water and methylene chloride. This two-phase mixture was then treated with an excess of 1N NaOH. The aqueous phase was decanted, dried over $Na_2SO_4$, filtered and the filtrate was concentrated under reduced pressure. After recrystallization in pentane, the compound of formula (IV) was obtained of melting point 91°–2° C. (decomposition).

1.3. 2-(4-methylphenyl)-4,5-dihydroimidazo[1,2-a]-quinol-1-ylmethanol 4.62 g (0.0164 mol) of the compound obtained in 1.2. and 12.5 ml of 37% strength formaldehyde in water were dissolved in 62 ml of glacial acetic acid, and the mixture was heated for 4 hours 30 min to 50° C. The reaction mixture was concentrated under reduced pressure and the residue taken up with water and ammonia solution until its pH was at least 7. The compound obtained was extracted with methylene chloride. After drying and evaporation of the solvent, a beige solid was obtained of melting point 213.5°–216° C.

1.4. N-{[2-(4-methylphenyl) 9-4,5-dihydroimidazo[1,2-a]quinol-1-yl]methyl}butanamide 2.9 ml of concentrated sulphuric acid was added by drops to a suspension of 3.4 g of the compound obtained in 1.3. in 34 ml of butyronitrile, which was maintained at 50° C. The heating was progressively increased until an oil settled out. The excess butyronitrile was removed and the oil hydrolyzed and then treated with an excess of ammonia solution until it reached a basic pH. The compound obtained was extracted with methylene chloride and then purified by chromatography on silica, and finally recrystallized in ethyl acetate. Its melting point was 212°–213° C.

1.5. N-methyl-N-{[2-(4-methylphenyl)-4,5-dihydroimidazo[1,2-a]quinol-1-yl]methyl}butanamide.

2 g (0.0056 mol) of the amide obtained in 1.4. were suspended in a mixture of 40 ml of dry THF and 4 ml of dry DMF containing 0.560 g (2 equivalents) of 50% strength NaH in oil and 1.62 g (0.01 mol) of methyl iodide. This mixture was maintained with stirring until the evolution of gas had ceased, and was then treated with 1 ml of methanol. The reaction mixture was evaporated under reduced pressure, the residue taken up with water and the compound of formula (I) extracted with methylene chloride and purified by chromatography. It had a melting point of 110°–112° C.

EXAMPLE 2

N-methyl-N-{[2-(4-methylphenyl)imidazo[1,2-a]-quinol-1-yl]methyl}butanamide.

2.1. 1-[2-(4-methylphenyl)-2-oxoethyl]quinolinium bromide 110 g (0.516 mol) of α-bromo-para-methylacetophenone and 61 ml (0.516 mol) of quinoline were dissolved in 500 ml of methylene chloride. The solution was heated at the reflux temperature for 1 hour and then diluted with 300 ml of ether and cooled. The quaternary salt of formula (III) was obtained by filtration. It had a melting point of 220°–1° C.

2.2. 2-(4-methylphenyl)imidazo[1,2-a]quinoline

A mixture of 75 g (0.219 mol) of the salt obtained in 2.1., 102.5 g of ammonium acetate, 112.5 g of ferric chloride and 750 ml of propionic acid was heated at the reflux temperature for 24 hours. After cooling, the precipitate was filtered off and washed twice with 100 ml of acetic acid and then with water until the liquid which drained was colourless. The precipitate was suspended in water and treated with an excess of ammonia. The product was extracted with methylene chloride, the organic phase decanted, dried over MgSO4, filtered and the filtrate concentrated under reduced pressure. The evaporation residue was purified by chromatography. The product of formula (IV) melted at 118°–120° C.

2.3. 2-(4-methylphenyl)imidazo[1,2-a]quinol-1-ylmethanol.

7 g (0.027 mol) of the compound obtained in 2.2. was dissolved in 90 ml of acetic acid. 19 ml of 37% strength formaldehyde in water was added and the solution was heated to 60° C. for 3 hours. The acetic acid was evaporated off under reduced pressure and the residue treated with 100 ml of water and an excess of ammonia solution until the pH was at least 7. The compound was filtered off and washed with water and methylene chloride. After drying under vacuum, the alcohol of formula (V) was obtained, having a melting point of 287°–8° C.

2.4. N-{[2-(4-methylphenyl)imidazo[1,2-a]quinol-1-yl]methyl}butanamide.

2 g (0.0069 mol) of the alcohol obtained in 2.3. was suspended in 20 ml of butyronitrile. 1.72 ml (3.4 g) of concentrated sulphuric acid was slowly added by drops at a temperature not exceeding 10° C. The mixture was allowed to return to room temperature, and then heated to 65° C. and allowed to cool. The excess butyronitrile was removed and the solid treated with 50 g of ice followed by an excess of NH4OH until a basic pH was reached. The precipitate was filtered off, washed with water until the pH was neutral, with acetone, with ether and then dried. After recrystallization in nitromethane, the compound of formula (I) in which $R_1$ was hydrogen was obtained. The melting point was 238°–9° C.

2.5. N-methyl-N-{[2-(4-methylphenyl)imidazo[1,2-a]quinol-1-yl]methyl}butanamide.

A mixture of 2 g (0.0056 mol) of the compound obtained in 2.4. and 1.59 g (0.011 mol) of methyl iodide dissolved in 10 ml of THF/DMF (90:10) was added to a mixture of 50 ml of THF and 5 ml of dry DMF containing 0.56 g (0.011 mol) of 50% strength NaH in oil. When the evolution of gas had ceased, stirring was maintained for 1 hour. The reaction mixture was treated with 1 ml of methanol and the solvent was evaporated off. The residue was taken up with water and methylene chloride. The organic phase was decanted and dried over Na2SO4 and then filtered and evaporated under reduced pressure. The residue was purified by chromatography on silica. After drying, the compound of formula (I) was obtained. It had a melting point of 147°–49° C.

TABLE 1

| Compound | A | B | Y | X | $R_1$ | $R_2$ | M.p.(°C.) |
|---|---|---|---|---|---|---|---|
| 1 | H | H | H | 4-CH3 | H | CH3 | 229–231 |
| 2 | H | H | H | 4-CH3 | CH3 | CH3 | 144–145 |
| 3 | H | H | H | 4-CH3 | H | nC3H7 | 212–213 |
| 4 | H | H | H | 4-CH3 | CH3 | nC3H7 | 110–112 |
| 5 | H | H | H | 4-CH3 | H | iC4H9 | 204–206 |
| 6 | H | H | H | 4-CH3 | CH3 | iC4H9 | 89–91 |
| 7 | H | H | H | 4-Cl | H | nC3H7 | 209–211 |
| 8 | H | H | H | 4-Cl | CH3 | nC3H7 | 76–77 |
| 9 | H | H | H | 4-Cl | H | iC4H9 | 206–207 |
| 10 | H | H | H | 4-Cl | CH3 | iC4H9 | 91–93 |
| 11 | H | H | H | 4-SCH3 | H | iC4H9 | 207–209 |
| 12 | H | H | H | 4-SCH3 | CH3 | iC4H9 | 92–93 |
| 13 | — | | H | 4-CH3 | H | CH3 | 275–277 |
| 14 | — | | H | 4-CH3 | CH3 | CH3 | 137–138 |
| 15 | — | | H | 4-CH3 | H | nC3H7 | 238–239 |
| 16 | — | | H | 4-CH3 | CH3 | nC3H7 | 147–149 |
| 17 | — | | H | 4-CH3 | H | iC4H9 | 246–247 |
| 18 | — | | H | 4-CH3 | CH3 | iC4H9 | 105–106 |
| 19 | — | | H | 4-Cl | H | CH3 | 289–290 |
| 20 | — | | H | 4-Cl | CH3 | CH3 | 179–181 |
| 21 | — | | H | 4-Cl | H | nC3H7 | 270–271 |
| 22 | — | | H | 4-Cl | CH3 | nC3H7 | 166–167 |
| 23 | — | | H | 4-Cl | H | iC4H9 | 263–265 |
| 24 | — | | H | 4-Cl | CH3 | iC4H9 | 138–140 |
| 25 | — | | H | 4-Cl | H | nC5H11 | 218–219 |
| 26 | — | | H | 4-Cl | CH3 | nC5H11 | 143–145 |
| 27 | — | | H | 4-SCH3 | H | nC3H7 | 252–253 |
| 28 | — | | H | 4-SCH3 | CH3 | nC3H7 | 149–150 |
| 29 | — | | H | 4-SCH3 | H | iC4H9 | 241–242 |
| 30 | — | | H | 4-SCH3 | CH3 | iC4H9 | 170–172 |
| 31 | — | | H | 4-NO2 | H | iC4H9 | 261–262 |
| 32 | — | | H | 4-NO2 | CH3 | iC4H9 | 227–228 |

The compounds of the present invention as defined in Table 1 (with reference to formula (I)) above were subjected to pharmacological trials to demonstrate their therapeutic activities.

Antagonism towards clonic convulsions induced by Cardiazol (Trade Mark) in mice

A trial, which was modelled on the procedure described by Goodman et al., J. Pharm. Exp. Ther., 108, 168–176, was carried out on mice. Mice either received the test products, or, as a control, the solvent alone, intraperitoneally 30 minutes before the intravenous injection of 35 mg/kg of Cardiazol. The animals were observed for one hour and, for each batch, the percentage of mice showing clonic convulsions was noted (100% of clonic convulsions and 10 to 20% of tonic convulsions in the control animals).

For each dose, the percentage protection relative to the control animals was calculated, and the $AD_{50}$, the dose which protects 50% of the animals as regards the convulsant effects of Cardiazol, was determined graphically. The $AD_{50}$ values of the compounds of the invention are from 0.1 to 30 mg/kg intraperitoneally and from 0.1 to 30 mg/kg orally.

"Burying" test in mice

A test which was modelled on the method described by Pinel J. P. J., Treit D., Ladak F. and MacLennan A. J. in Animal learning and behavior, 8, 447–451, (1980) was carried out.

The presence of foreign bodies in the usual environment of an animal represents an aversive situation, to which the animal reacts by burying the subject of the attack (in this case glass balls in the sawdust in its cage).

Anxiolytic substances reduce the apprehension caused by the presence of the foreign bodies and the animals engage in less burying.

The test products were administered to male CD1 strain mice (Charles River) 30 minutes (intraperitoneally) or 60 minutes (orally) before they were placed in cages containing 25 glass balls. After 30 minutes, the number of balls remaining unburied was counted and a percentage calculated between the treated animals and the control animals.

The $AD_{50}$, the 50% active dose, which is the dose of compound (in mg/kg) which reduces by one half the number of balls buried, by comparison with the control animals, was determined in this manner. The $AD_{50}$ values of the compounds of the invention are from 0.3 to 30 mg/kg intraperitoneally.

Drinking conflict test in rats

This test is described by Vogel J. R., Beer B. and Clody D. E. in Psychopharmacologia, 21, 1–7, (1971).

Male Wistar rats (IFFA Credo) were used. Their drinking water was withdrawn 24 hours before the test. On the day of the test, 30 minutes after intraperitoneal treatment with the compounds of the invention, each rat was placed in a transparent plastic cage (24×20×21 cm) having a meshwork floor which could be electrified. Drinking water was distributed via a pipette projecting 2 cm from one wall of the cage and placed 3 cm above the floor of the cage.

After exploration for from 10 to 90 seconds, the rats found the pipette and started to drink. After giving 20 licks with the tongue (recorded by an Omnitech (Trade Mark) anxiometer), the rat received an electric shock of 0.07 mA applied to its tongue (delivered by the anxiometer), which stopped when the rat left the pipette. This test then continued for 3 minutes after the first shock; the animals received a shock every 20 licks until they stopped or until the end of the session.

Under these experimental conditions, the control animals accepted, on average, 3 to 6 shocks. The number of shocks obtained with the treated animals was noted, and this number was compared with that of the control animals by a Dunett test. The MED, the minimal effective dose, which is the first dose which significantly increases the number of shocks accepted by an animal relative to the control animals, was determined in this manner.

The MED values are from 3 to 100 mg/kg intraperitoneally.

Action on the electrocorticogram of ventilated curarized rats

The sedative or hypnotic activity of the compounds was determined by observing their action on the electrocorticogram of rats according to the method described by H. Depoortere, Rev. E.E.G. Neurophysiol., 10, 3, 207–214 (1980) and by H. Depoortere and M. Decobert, J. Pharmacol. (Paris), 14, 2, 195–265 (1983).

The test compounds were administered intraperitoneally at increasing doses of from 1 to 30 mg/kg. They induced sleep traces with doses ranging from 3 to 100 mg/kg.

Koster's test

The analgesic activity was shown using the test of Koster et al. (acetic acid "writhing" test in mice), Fed. Proc., 18, 412, 1959.

The test compound, dissolved in Tween 80 (Trade Mark) at a concentration of 1%, was administered orally to fasted mice in a proportion of 0.2 ml per 20 g of body weight. After 30 min, acetic acid (dissolved at a concentration of 0.6% in a mixture of carboxymethylcellulose and Tween 80, in a proportion of 10 ml per kg of body weight) was administered intraperitoneally. The total number of contortions was noted during 15 min.

The percentage protection relative to a control batch was determined, and the $AD_{50}$ was calculated graphically (dose which protects 50% of the animals).

The $AD_{50}$ of the compounds of the invention ranges from 5 to 50 mg/kg p.o.

Stress ulceration inhibition test

The test used the technique described in Senay and Levine, Proc. Soc. Exp. Biol. 1967, 124, 1221–1223, Peptic Ulcers, on female Wistar rats weighing 180–210 g, kept fasted for 20 hours and distributed in randomized groups.

The animals were held in restraint in cylindrical boxes 20 cm×5 cm, and placed in a cold room at from 2° to 4° C.

The test compounds were administered orally in the proportion of 10, 30 and 100 mg/kg immediately before the restraint; the control rats received only placebo. 2 hours later, the animals were sacrificed by inhalation of chloroform.

The stomachs were removed and the degree of ulceration was noted.

The compounds of the invention significantly decreased the amount of stress ulceration.

The results of these different tests show that the compounds of the invention possess at least one anxiolytic, sleep-inducing, hypnotic, anticonvulsant, analgesic or antiulcerative property; the compounds of the invention are, for example, useful in the treatment of anxiety states, sleep disorders and other neurological and psychiatric conditions, disorders of alertness, and can be especially useful for combatting behavioural disorders ascribed to cerabral vascular damage and to cerebral sclerosis in geriatrics, for treating temporary loss of consciousness due to cranial trauma and for treating metabolic encephalopathies, as well as for treating aches, pain and ulcers.

The compounds of the invention can be presented in any form suitable for oral or parenteral administration, for example in the form of tablets, dragees, gelatin capsules, solutions to be taken by mouth or injectable solutions, in combination with any pharmaceutically acceptable excipient. The daily dosage can range from 1 to 100 mg.

We claim:

1. A compound which is a 1-acylaminomethylimidazo[1,2-a]quinoline of formula (I)

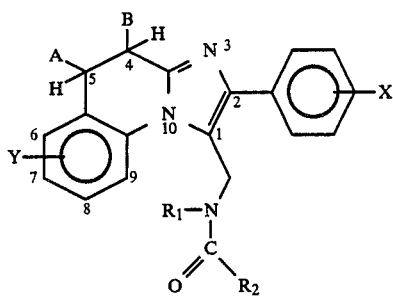

in which

A and B both denote hydrogen or together denote a direct carbon-carbon bond,

X denotes hydrogen or a halogen or a $(C_{1-4})$alkyl, $(C_{1-4})$alkoxy, $(C_{1-4})$alkylthio, methylsulphonyl, amino, $(C_{1-4})$alkylamino, di$(C_{1-4})$alkylamino, nitro or trifluormethyl group, Y denotes hydrogen or a halogen or a methyl group and is attached to the aryl ring at position 6, 7 or 8, $R_1$ denotes hydrogen or a $(C_{1-4})$alkyl group, and $R_2$ denotes a $(C_{1-6})$alkyl group, or a pharmaceutically acceptable acid addition salt thereof.

2. A compound according to claim 1, wherein X denotes chlorine, or a methyl or methylthio group, Y denotes hydrogen and $R_1$ denotes hydrogen or a methyl group.

3. An anticonvulsant, composition, comprising an effective anticonvulsant amount of a compound claimed in claim 1 and a pharmaceutically acceptable excipient.

4. A composition according to claim 3 in unit dosage form containing from 1 to 100 mg of the compound of formula (I).

5. A sleep-inducing or hypnotic composition comprising an effective sleep-inducing amount of a compound claimed in claim 1 and a pharmaceutically acceptable excipient.

6. An anxiolytic or anti-stress ulcer composition comprising an effective anxiolytic amount of a compound as claimed in claim 1 and a pharmaceutically acceptable excipient.

7. An analgesic composition comprising an effective analgesic amount of compound as claimed in claim 1 and a pharmaceutically acceptable excipient.

8. A composition according to claim 5 in unit dosage form having from 1 to 100 mg of the compound of formula (I).

9. A composition according to claim 6 in unit dosage form having from 1 to 100 mg of the compound of formula (I).

10. A composition according to claim 7 in unit dosage form having from 1 to 100 mg of the compound of formula (I).

* * * * *